United States Patent
Freathy

(10) Patent No.: US 9,563,995 B2
(45) Date of Patent: Feb. 7, 2017

(54) WIRELESS TAG AND HOME MONITORING DEVICE FOR TRACKING INDIVIDUALS OR OBJECTS WITH ALCOHOL MONITORING

(71) Applicant: Satellite Tracking of People LLC, Houston, TX (US)

(72) Inventor: Stephen Freathy, Houston, TX (US)

(73) Assignee: SATELLITE TRACKING OF PEOPLE LLC, Houston, TX (US)

( * ) Notice: Subject to any disclaimer, the term of this patent is extended or adjusted under 35 U.S.C. 154(b) by 0 days.

(21) Appl. No.: 14/269,367

(22) Filed: May 5, 2014

(65) Prior Publication Data

US 2014/0347187 A1 Nov. 27, 2014

Related U.S. Application Data

(60) Provisional application No. 61/819,088, filed on May 3, 2013.

(51) Int. Cl.
| | |
|---|---|
| *G08B 23/00* | (2006.01) |
| *G07C 9/00* | (2006.01) |
| *G08B 21/22* | (2006.01) |
| *A61B 5/11* | (2006.01) |
| *A61B 5/00* | (2006.01) |
| *A61B 5/022* | (2006.01) |

(52) U.S. Cl.
CPC .......... *G07C 9/00111* (2013.01); *A61B 5/1112* (2013.01); *A61B 5/4845* (2013.01); *G08B 21/22* (2013.01); *A61B 5/022* (2013.01); *A61B 2505/07* (2013.01)

(58) Field of Classification Search
CPC ..... G08B 21/22; G08B 21/02; G08B 21/0269; G08B 21/0461
USPC .......................................... 340/539.15, 573.4
See application file for complete search history.

(56) References Cited

U.S. PATENT DOCUMENTS

| | | | | |
|---|---|---|---|---|
| 6,054,928 A | * | 4/2000 | Lemelson .......... | G08B 21/0233 340/539.1 |
| 7,522,060 B1 | * | 4/2009 | Tumperi ................ | G06Q 10/06 340/5.82 |
| 2012/0232749 A1 | * | 9/2012 | Schoenberg .......... | B60N 2/002 701/36 |

(Continued)

*Primary Examiner* — Kerri McNally
*Assistant Examiner* — Sharmin Akhter
(74) *Attorney, Agent, or Firm* — Polsinelli PC

(57) ABSTRACT

A methodology determining a response to exposure of a monitored person to a prohibited substance is provided. The methodology includes: first receiving movement data representing movement of the monitored person over time; second receiving an indication that a monitored person has been exposed to a quantity of a prohibited substance; first determining, from the received movement data, movement activity of the monitored person for a period of time before the exposure was detected; second determining a risk parameter based on at least (a) the amount of the quantity of the prohibited substance, and (b) the movement activity; issuing a notice to a supervising authority in substantially real time when the second determining results in a risk parameter that is above a first threshold; and issuing a notice to a supervising authority in non-real time when the second determining results in a risk parameter that is below the first threshold.

15 Claims, 8 Drawing Sheets

(56) References Cited

U.S. PATENT DOCUMENTS

2014/0375462 A1* 12/2014 Biondo .................. A61B 5/18
340/576

* cited by examiner

WIRELESS TAG AND HOME MONITORING DEVICE FOR TRACKING INDIVIDUALS OR OBJECTS WITH ALCOHOL MONITORING

CROSS REFERENCE TO RELATED APPLICATIONS

The instant application claims priority to U.S. Provisional Application 61/819,088 filed May 3, 2013 entitled WIRELESS TAG AND AUXILIARY DEVICE FOR USE WITH HOME MONITORING UNIT FOR TRACKING INDIVIDUALS OR OBJECTS WITH ALCOHOL MONITORING, the contents of which are herein incorporated by reference in its entirety.

FIELD OF THE INVENTION

The various embodiments described herein relate generally to provide locational tracking of a portable monitoring device attached to a monitored individual, substance screening for the monitored individual, and related reporting services. More specifically, the various embodiments herein relate to monitoring the movement of a monitored individual relative to their exposure to prohibited substances.

BACKGROUND

The monitoring of movements of monitored individuals involves a variety of sectors, including parolees and home confinement. The technology has its roots in the home arrest systems of the 1980's, in which a user wearable component—typically a "beacon" anklet that was locked to the monitored person, would communicate wirelessly with a stationary base unit. The range was limited to a few feet of the radio frequency transmitter and receiver. The base unit included a telephone connection for communicating with the authorities. If the monitored person left the short range allowed by the equipment, the tag and the base unit would lose contact and the base unit would respond by sending an alert to the authorities.

A later generation of the technology incorporated GPS and cellular telephone technology in a locked anklet. The device would actively monitor the location of the monitored person over time and transmit the data to a central monitoring location (e.g., police or parole monitoring services). The central location could store and analyze the data for prohibited movements (e.g., a sex offender near a school) or cross reference the movement data with crime data to see if the monitored person was near the crime at the time of the crime. U.S. Pat. Nos. 5,867,103, 6,160,481, 6,218,945, 6,512,456 and 6,703,936, incorporated herein by reference in their entireties, are exemplary of such a system.

A later generation of the technology hybridized the beacon technology and the GPS technology. The system included both an anklet with GPS and cellular communications, along with a short range modem. A fixed base unit at a fixed location (typically the monitored person's residence) could communicate with the ankle when within range of the short range modem. When the anklet was remote from the fixed location, the anklet could operate independently and communicate with the central monitoring location. When it was within range of the fixed location, the anklet could cooperate with the fixed unit. For example, the anklet could discontinue use of its cellular modem in favor of lower power communication with the fixed unit; the fixed unit could then relay the information to the central monitoring location through wired or wireless communication. U.S. Pat. No. 8,334,769, incorporated herein by reference in its entirety, is exemplary of such a system.

Alcohol and substance abuse monitoring has been incorporated into the anklet. Since the anklet worn about the ankle is not accessible by mouth to conduct breathalyzer tests, various technologies monitor the presence of prohibited substances in the sweat of the skin. These technologies are not as effective as breathalyzer tests, as there can be a delay between consumption of a prohibited substance and appearance of the substance in the sweat. Physical obstacles (e.g., a sock) or other chemical skin treatments could interfere with skin based detection and/or require dedicated countermeasures.

BRIEF DESCRIPTION OF THE DRAWINGS

Various embodiments in accordance with the present disclosure will be described with reference to the drawings, in which.

DETAILED DESCRIPTION

In the following description, various embodiments will be illustrated by way of example and not by way of limitation in the figures of the accompanying drawings. References to various embodiments in this disclosure are not necessarily to the same embodiment, and such references mean at least one. While specific implementations and other details are discussed, it is to be understood that this is done for illustrative purposes only. A person skilled in the relevant art will recognize that other components and configurations may be used without departing from the scope and spirit of the claimed subject matter.

Figure 1:
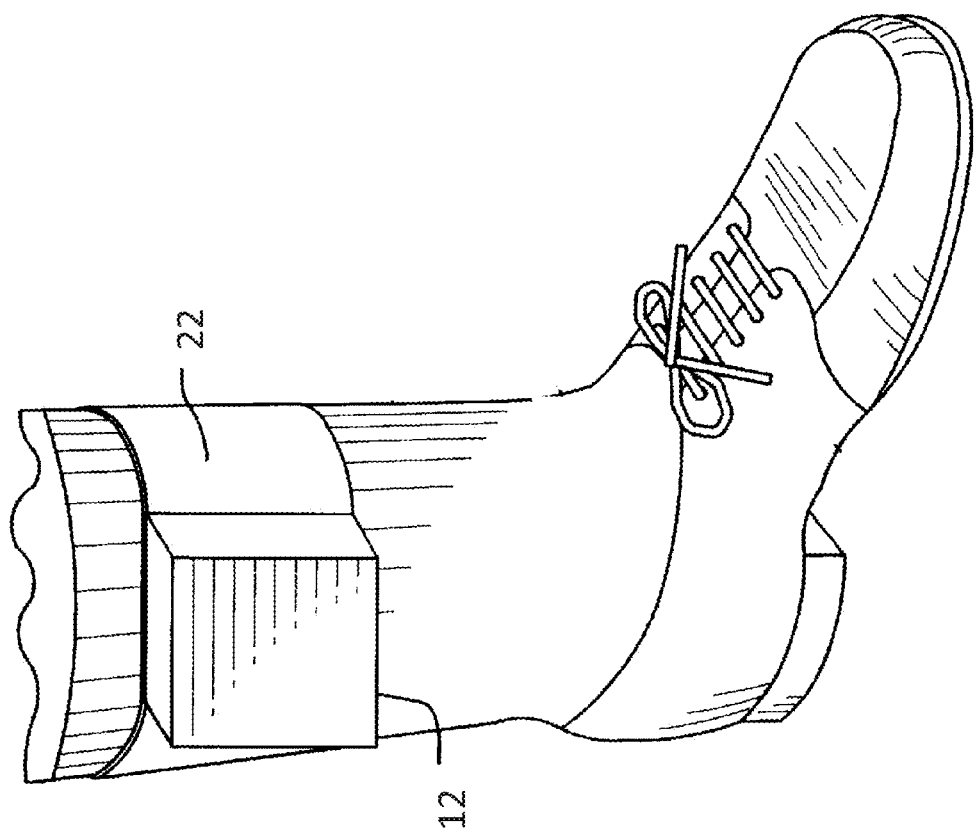
FIG. 1 illustrates an embodiment of the invention in which a personal monitoring device is mounted on an ankle of a monitored person.

FIG. 1 shows a block diagram of a monitoring system 10 according to an embodiment of the invention. A personal monitoring device 12 can determine its location, such as through the Global Positioning Satellite, cell towers, LORAN, or other known methodologies; for sake of brevity discussion herein is confined to GPS, although the invention is not so limited.

A band 22 secures personal monitoring device to a limb of the user, typically the ankle, via a locking mechanism that preferably can only be opened by an authorized person. An ankle is shown in FIG. 1, although the invention is not limited thereto. Personal monitoring device 12 and band 22 preferably have tamper detection capabilities as is known in the art and not discussed further herein. The invention is not limited to any particular securing and/or tamper detection methodology.

An authorized person would be one or more people having some type of supervisory responsibility and/or decision making relative to the monitored person. A non-limiting example, a parole officer while the monitored individual is a parolee. Other non-limiting examples include parent/child, patient/medical supervisor, etc. Security and/or police could be considered authorized person to the extent the emergency level intervention is necessary. For sake of brevity discussion herein is confined to parolee/parole officer relationship, although the invention is not so limited.

Figure 2:
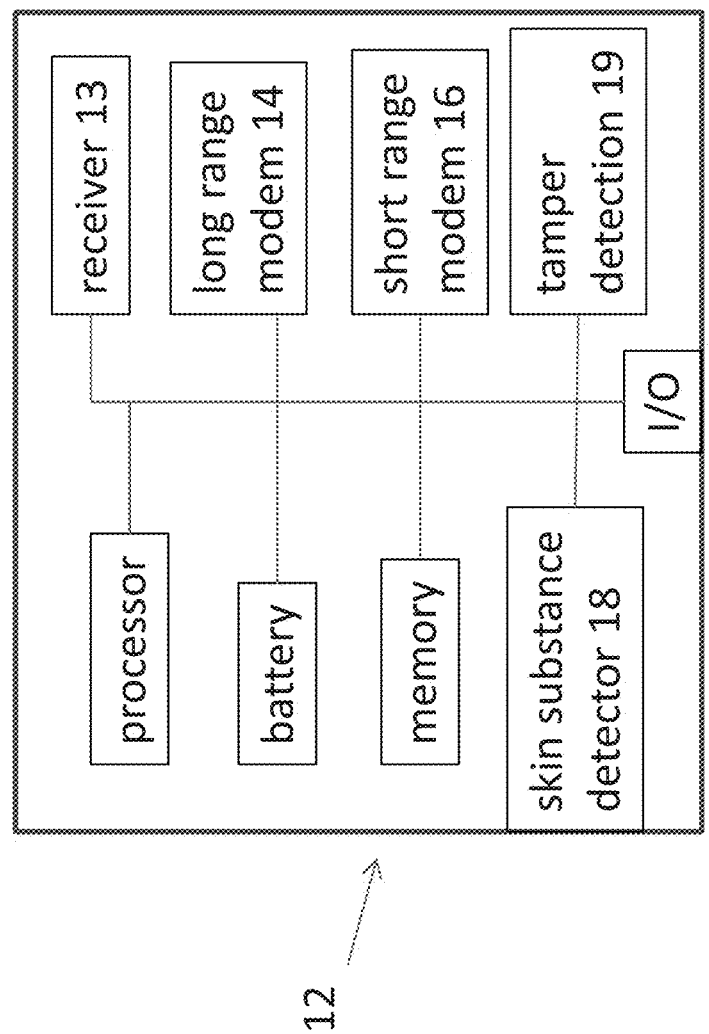
FIG. 2 illustrates a black box drawing of the components of an embodiment of a personal monitoring device.

Referring now to FIG. 2, preferably the personal monitoring device 12 includes a dedicated circuit for determining its location, such as a GPS receiver chip 13. A cellular modem 14 preferably provided with a SIM card allows the personal monitoring device 12 to communicate through the cellular network with a central monitoring station 40. A short range wireless modem 16 (e.g., 915 MHz or 802.11 compatible Wi-Fi or Bluetooth) allows the personal monitoring device 12 to communicate locally with other devices within the short range as is known in the art for such devices. Modems 14 and 16 may be the same modem operable to communicate on different frequencies. A substance detector 18 may be provided to monitor the presence of prohibited substances in the monitored individual, such as through a sensor in contact with the skin; the configuration of substance detectors within a portable monitored device are known by those of skill in the art and not further discussed herein. Tamper detection mechanism 19 monitors for tamper detection as is known in the art. Batteries, a power port, memory, I/O interface, wired communication access and other supporting computer hardware and software as is known in the art are also preferably provided and not discussed further herein. Personal monitoring device 12 may be integrated into a single unit or multiple units as is known in the art. The invention is not limited to the details of the architecture of personal monitoring device 12.

Figure 3:
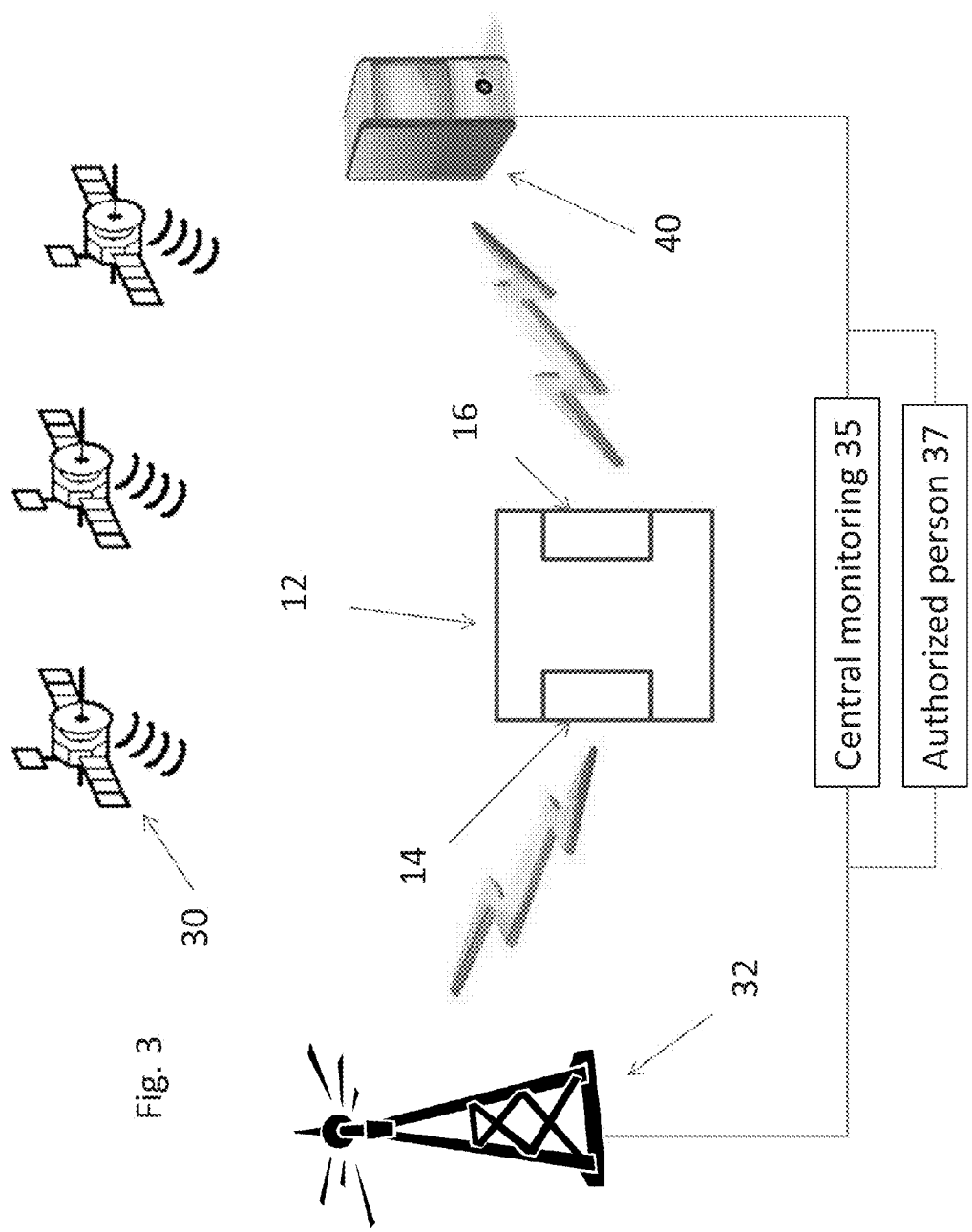
FIG. 3 illustrates an operating environment of a personal monitoring device and a home monitoring device according to an embodiment of the invention.

Referring now to FIG. 3, personal monitoring device 12 is shown in an operating environment. Multiple satellites 30 provide the GPS timestamps that GPS receiver 13 in personal monitoring device 12 converts into location information. The location information represents the location of the personal monitoring device 12, and by extension the location information for the monitored individual, at a particular time. Personal monitoring device 12 can transmit that information in near real time, and/or can store the location information in memory and batch transfer collected location information as dictated by the need of the system (e.g., on a fixed and/or random schedule, or in response to an event or specific instruction to do so). If substance detection capability is present, then information relating to screening(s) may be similarly stored, transmitted in near real time or batch transmitted collectively, either with or separately from the movement information Personal monitoring device 12 preferably has at least two options for remote communications, including data transfer. The first is through the short range modem 16 with a home monitoring device 40 when within the range (e.g., <300 feet, more particularly about 50-100 feet) of the short range modem 16. The second is through the cell/long range modem 14 (potentially miles) to a cell tower 32 when the personal monitoring device is out of range of the home monitoring device 40. Preferably both cell tower 32 and home monitoring device 50 connect to central monitoring location 35 and/or an authorized person 37, whether directly or through intervening equipment as known in the art. In theory short range modem could also connect with other short range devices (e.g., typical Internet hotspots), but the lack of trusted status may limit access to, or execution of, some of the functionality described herein.

Central monitoring location 35 is "central" in the sense that it serves one or more personal monitoring devices 12. It may be a single location, multiple locations operating independently, or a distributed arrangement. At a most basic level the central monitoring station is no more than a computer (e.g., a server) having a memory, processor, modem, input/output, and other supporting computer hardware and software as is known in the art, although in practice they may be large facilities with distributed computers and human handlers. The invention is not limited to the architecture or layout of the central monitoring location 35.

The details regarding how the personal monitoring device 12 can leverage the two available communication pathways to the central monitoring location 35 and/or the authorized person 37 are set forth in U.S. Pat. No. 8,334,769, and is not discussed further herein.

Home monitoring device 40 is "home" in the sense that it is preferably located at a fixed physical location at which the monitored person frequents, such as their residence or place of employ. There is no limit to the number of home monitoring units, and in theory multiple units can be dispersed to provide comprehensive coverage over a large area. Home monitoring device 40 may be individually paired with a particular personal monitoring device 12, or with multiple devices that enter and leave the operating communication range.

Figure 4:
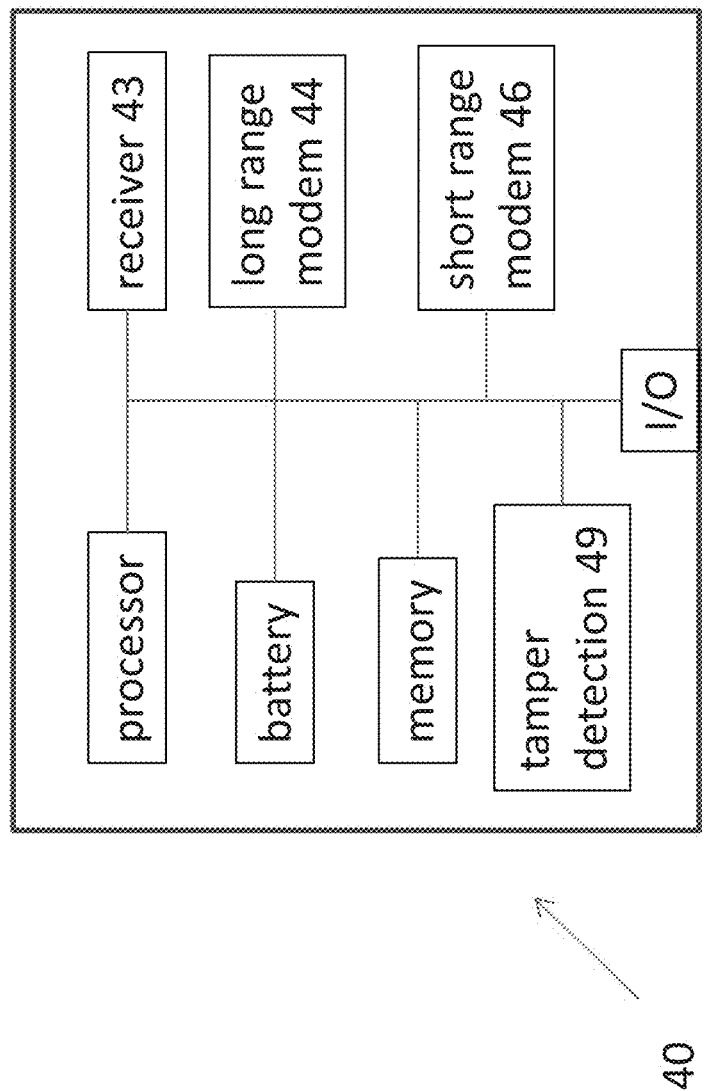
FIG. 4 illustrates a black box drawing of the components of an embodiment of a home monitoring unit.

FIG. 4 shows a black box drawing of home monitoring device 40. Home monitoring device 50 includes at least a short range wireless modem 56 for communicating with personal monitoring device 12. Home monitoring device 40 can also communicate with the central monitoring location 35 and/or authorized person 37, either through short range wireless modem 46 (to a nearby WiFi hot spot), a cell/long range modem 44, or a wired modem or phone land line connection (with the "I/O" port) or other wired or wireless connection. Home monitoring device 40 is not limited by the architecture or methodology by which it can communicate with central monitoring location 35 or authorized person 37. Local monitoring device preferably includes tamper detection capabilities (such as tamper detection mechanism 49) and movement detection capabilities as is known in the art. A receiver element 43, such as a GPS receiver, may be provided to allow home monitoring device 40 to determine its location. Batteries, a power port, memory, processor, interface, wired communication access and other supporting computer hardware and software as is known in the art are also preferably provided and not discussed further herein.

The personal monitoring device 12 communicates with the GPS network and a home monitoring device 40 to respectively obtain geographic location information and to exchange data with the central monitoring location 35 and/or the authorized person 37. The central monitoring location monitors the location of the personal monitoring device 12 (as well as the object or individual attached thereto) and compares the monitored location to a database of acceptable and unacceptable location and time parameters. The personal monitoring device 12 generally transmits position data updates to the central monitoring location 35, either directly or through home monitoring device 40 (inclusive of intervening equipment as necessary, such as the cell network).

Home monitoring device 40 and personal monitoring device 12 are considered in operating range of each other when they establish an operational connection via their modems, preferably a stable connection. The relationship is thus limited to the distance allowed by the modems, the underlying protocols (e.g. 802.11 or 915 MHz), and any intervening or interfering conditions (e.g., walls, local electromagnetic sources). When in a stable relationship, the personal monitoring device 12 is "tethered" to the home monitoring device 12, as the monitored person is known to be at a location that is within the range of the mutual modems.

The above description and operating of the personal monitoring device 12 and the home monitoring device 40 may be consistent with the disclosure of U.S. Pat. No. 8,334,769.

Figure 5:
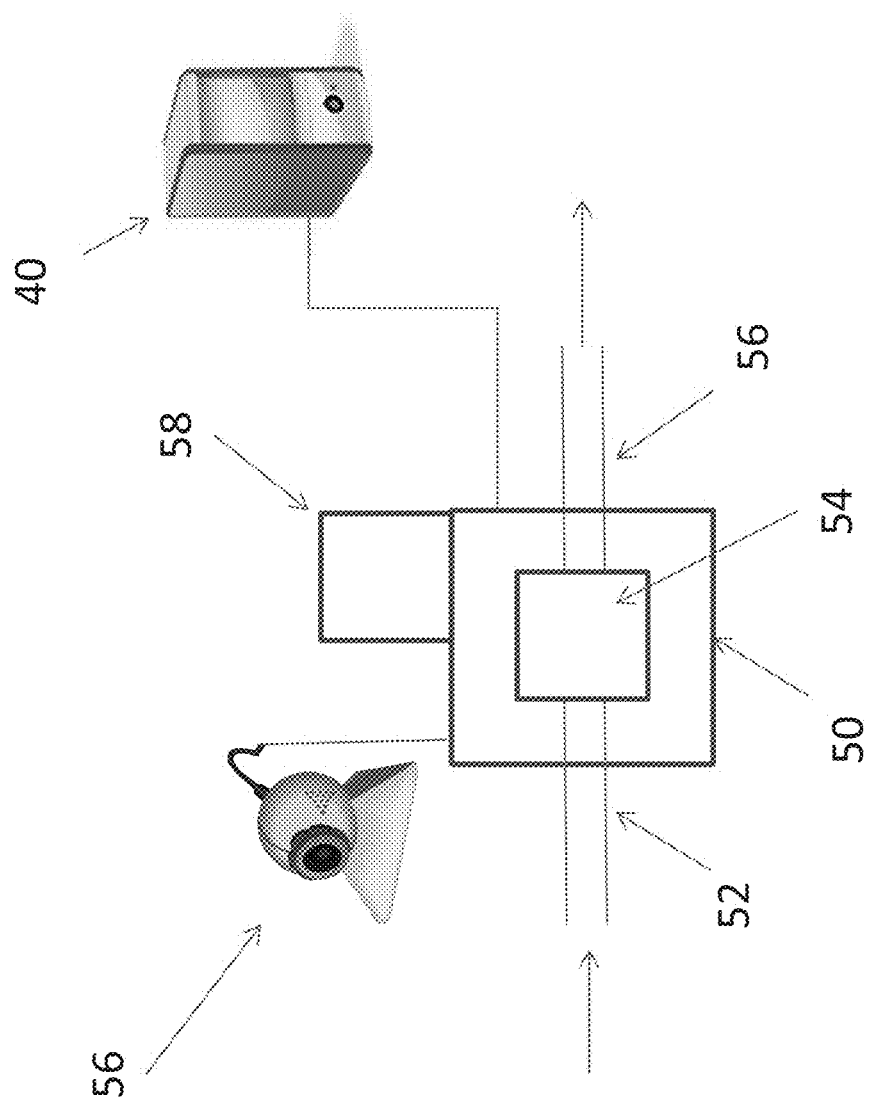
FIG. 5 illustrates an operating embodiment and components for a prohibited substance detection device.

Referring now to FIG. 5, a prohibited substance detection device 50 is associated with home monitoring device 20. The architecture and methodology of prohibited substance detection device may be entirely incorporated into home monitoring device 40, partially incorporated, or entirely separate and in communication therewith through wired or wireless connection as is known in the art. For purposes of brevity the description below is directed toward an entirely separate device, but the invention is not so limited.

Prohibited substance detection device 50 includes breathalyzer based components for determining from the breath whether an individual has been exposed to or consumed prohibited substances. Prohibited substance detection device includes an air inlet 52, an air outlet 56, and a substance detection unit 54 to define an air flow pathway. A user blows air into the pathway, and the substance detection unit 54 analyzes the air flowing through for the presence of prohibited substances. The architecture of such breath analysis equipment is known in the art and not described further herein. In addition and/or the alternative, other types of prohibited substance detection methodologies may be used, such as a sweat sensor or blood sample testing kit, whose architecture is also known in the art and not described further herein.

Prohibited substance detection device 50 preferably includes a camera 56, which can be used to provide a video feed of the monitored individual performing the prohibited substance screening. This video, which can be stored and/or transmitted, can be used to confirm the identity of the monitored individual taking the test as opposed to a sober friend), as well as video evidence to show when, where and how the screening was conducted. In addition and/or in the alternative, one or more biometric sensors 58 (e.g., fingerprint, DNA, retina match, etc.) could be provided to confirm the identity of the monitored person during the screening. A display, speakers and/or microphone may also be available to provide information or instructions (e.g. blow harder, pass/fail) to the test taker and/or allow communication with a monitoring authority.

Prohibited substance detection device 50 preferably leverages the tamper detection mechanism 49 of home monitoring unit 40, or has its own dedicated mechanism.

Prohibited substance detection device 50 may store the screening data (e.g., the identity of the monitored individual, the tests applied, detected substances, amounts of detected substances, video feed, biometric sensor read, etc.) in memory and/or transmit the screening data in real time to the central monitoring location 35 and/or authorized person 37. In the alternative, the screening data can be stored in memory and collectively batch transferred at a later time based on a schedule and/or a specific triggering event (such as a tamper detection alert, low power alert, entering the range of a home monitoring unit 40). Screening data may be sent with or separately from movement data. Screening data may also be sent in part(s) and retained in part.

When the monitored person is out of range of the home monitoring device 40, the system recognizes that screening is not possible at that location at that time. When the monitored person enters the range of home monitoring device 40, substance detection protocols can engage. Protocols may be implemented directly by home monitoring device 50 and/or by command from central monitoring location 35. By way of example, the home monitoring device 40, the central monitoring location 35 and/or authorized person 37 can instruct the monitored person through appropriate signal (e.g., call, email, SMS, or signal to personal monitoring unit 12) to submit to a substance abuse screening at the home monitoring device 40 within five minutes of establishing a stable connection. Screenings can be scheduled, random, voluntary, or a combination thereof.

The system may be dynamic to react to failures to adjust testing parameters. For example, if the offender is failing more often between 7-11 PM than other times, the system may add tests or adjust the timing of tests at either personal monitoring device 12 and/or prohibited substance detector 50 so that testing occurs more frequently in that time frame.

By limiting substance screening to when the monitored person is proximate to the home monitoring device 40, the system places less stress and resources on the individuals involved. For the monitored person, they are not concerned that they will be required to perform a screening when they cannot get to home monitoring device 40 and risk a fail (although a monitored person that is on a required schedule and fails to appear for a test may face a related problem). Similarly, the central monitoring location 35 and/or the authorized person 37 will not receive needless alerts that might otherwise distract from better allocation of oversight resources.

According to another embodiment of the invention, the personal monitoring device 12 may have various operating modes based on whether or not the personal monitoring device 12 is in range of home monitoring device 40. For example, the personal monitoring device 12 may have a schedule for conducting and/or reporting screenings. When personal monitoring device 12 is remote from home monitoring device 40, it has no backup for screening, and thus could have a rigid schedule, such as once per hour. When personal monitoring device 12 is within range of the home monitoring device 40, then at least some of the screening responsibilities can be taken over by the prohibited substance device 50. Personal monitoring device 12 can thus reduce screening operations, such as by reducing the frequency of screening (including reducing to zero), changing the type of screening (e.g., if both skin and breath screening is provided, reducing the breath screening in favor of such screening as may be provided by prohibited substance detection device 50), reducing the frequency of reporting, etc.

According to another embodiment of the invention, if the personal monitoring device 12 detects a prohibited substance through the skin, then home monitoring device 40 may respond by calling for an immediate breath test (instantly if within range, or upon entry of range if currently too far away). This could be instituted as an alert signal, or simple contents of transmitted data with a negative screening test result, from the personal monitoring device 12 to the home monitoring device 40 and/or the central monitoring location 35 (which could send an instruction to home monitoring device), As noted above, breath tests may provide different data than skin tests based upon the time it take to metabolize the substance.

Figure 6:
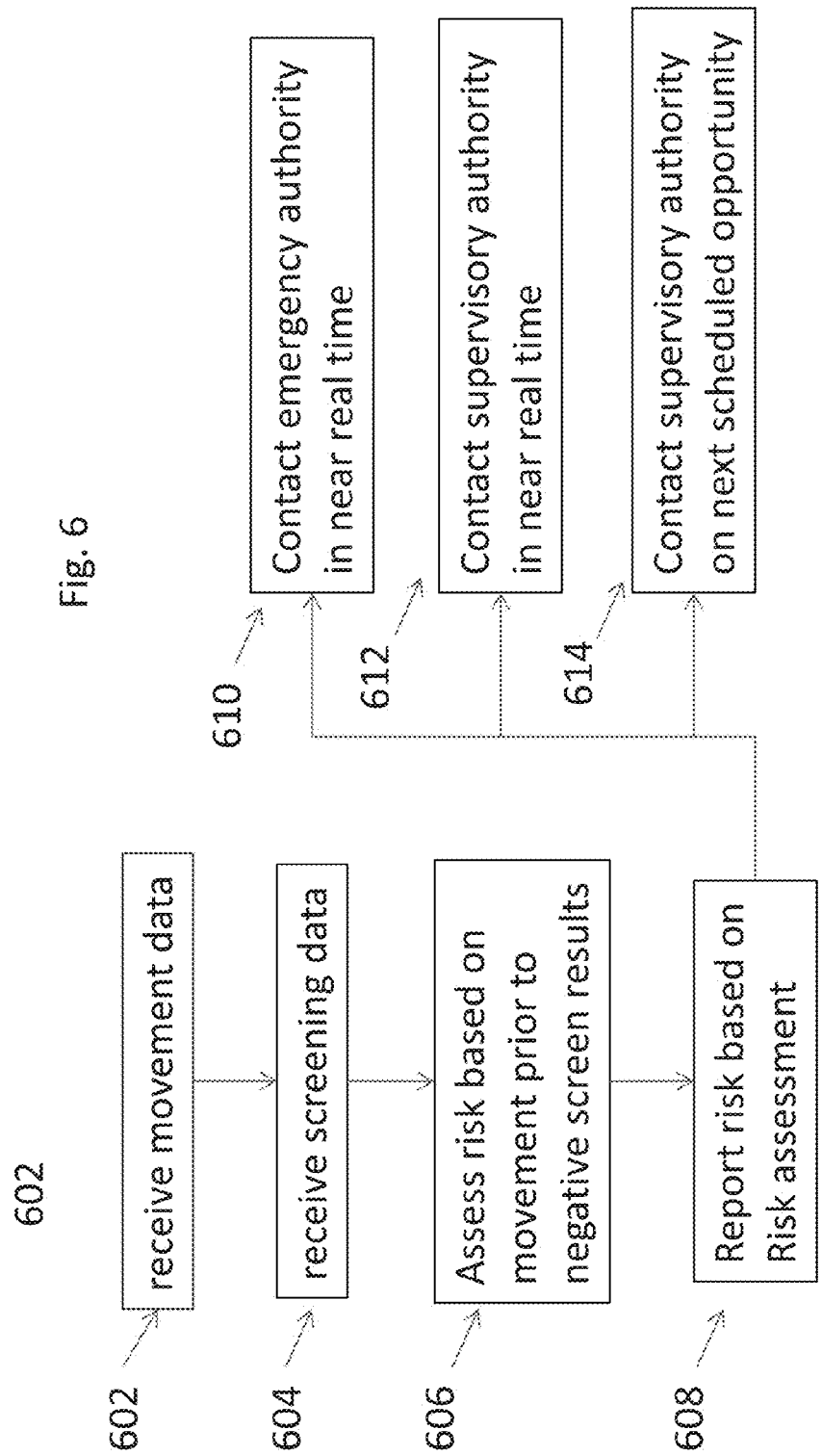
FIG. 6 illustrates a flowchart of operation of an embodiment of the invention.

Referring now to FIG. 6, according to another embodiment of the invention, the central monitoring location 35 receives processes substance screening data and movement data at steps 602 and 604, which may occur in any order or simultaneously. This data may be provided by the embodiments discussed above, or from other sources of information. The embodiment is not limited to where, when or how the data movement and screening data is received, although it is generally performed on electronic computer hardware in combination with appropriate software. Central monitoring location 35 is provided with typical computer equipment and software, including memory, processor, interfaces, etc. that are well known in the art. By way of non-limiting example, the methodology may be stored in memory and applied to received data in the processor.

Movement data is generally analyzed to determine any improper activity by the monitored person, e.g., entering restricted areas, deviating from allowed areas, being at the scene of a crime at the time of the crime, etc. Screening data may be considered in isolation. Preferably at step 606 the screening data may also be considered in combination with movement data to assess the risk posed by violations. By way of example, different substances and different quantities may raise different levels of risk, and corresponding alerts, based on where and when the occurred. Alert levels may translate into how the system reports out violations in step 608, and particularly on what schedule. A high level alert could trigger the central monitoring station in near real time to alert emergency authorities, such as local police or security, for immediate intervention at step 610. A moderate level alert might alter the supervisory authority, such as a parole officer, in near real time at step 612 for a more discretionary response. A low level alert may not require a near real time notice, and may thus only be reflected in scheduled (e.g. daily) reports at step 614, or even disregarded.

The management of the alert levels is of particular importance to avoid overtaxing the controlling authority. Too many alerts can desensitize the controlling authority for individual offenses, while too few alerts may present danger of an unaddressed problem. The controlling authority can set the parameters of alerts at levels that are both tolerable and effective for the particular jurisdiction. The additional use of movement data to augment or reduce alert levels based on screening data alone aids in striking that balance.

By way of non-limiting example, detecting the presence of alcohol with a blood concentration at 1.0—which is above the legal limit for driving—could be considered a particular alert level regardless of movement. However, a lower 0.5 blood concentration level could raise different concerns based on the movement history over a time period (e.g., 2 hours) before the negative test. It may be a lesser concern if the movement information indicates that the monitored individual has been at home as compared to away from home, as the former is a safer environment and the latter may suggest prohibited public activity. It may still be a significantly higher concern if the movement history indicates that the monitored individual was previously moving at high speeds consistent with driving, as thus may indicate drunk driving (either by the monitored person or others in the car). Movement date would establish where the monitored person was, and thus form a consideration on the alert level.

The system could be set to different levels of sensitive based on the desired preference of the system. Parameters and corresponding alert levels could be as follows by way of non-limiting example:

| Screening data | Movement Data | Violation/Alert level |
|---|---|---|
| *Cannabis* (any volume) | Not at home | High |
| *Cannabis* (any volume) | Home | Moderate |
| Alcohol > 1.0 | Any | High |
| 0.7 < Alcohol < 1.0 | Driving speed | High |
| 0.0 < Alcohol < 1.0 | Not at home | Moderate |
| 0.3 < Alcohol < 1.0 | Home | Low |
| Alcohol < 0.3 | Home | Disregard |

Figure 7:
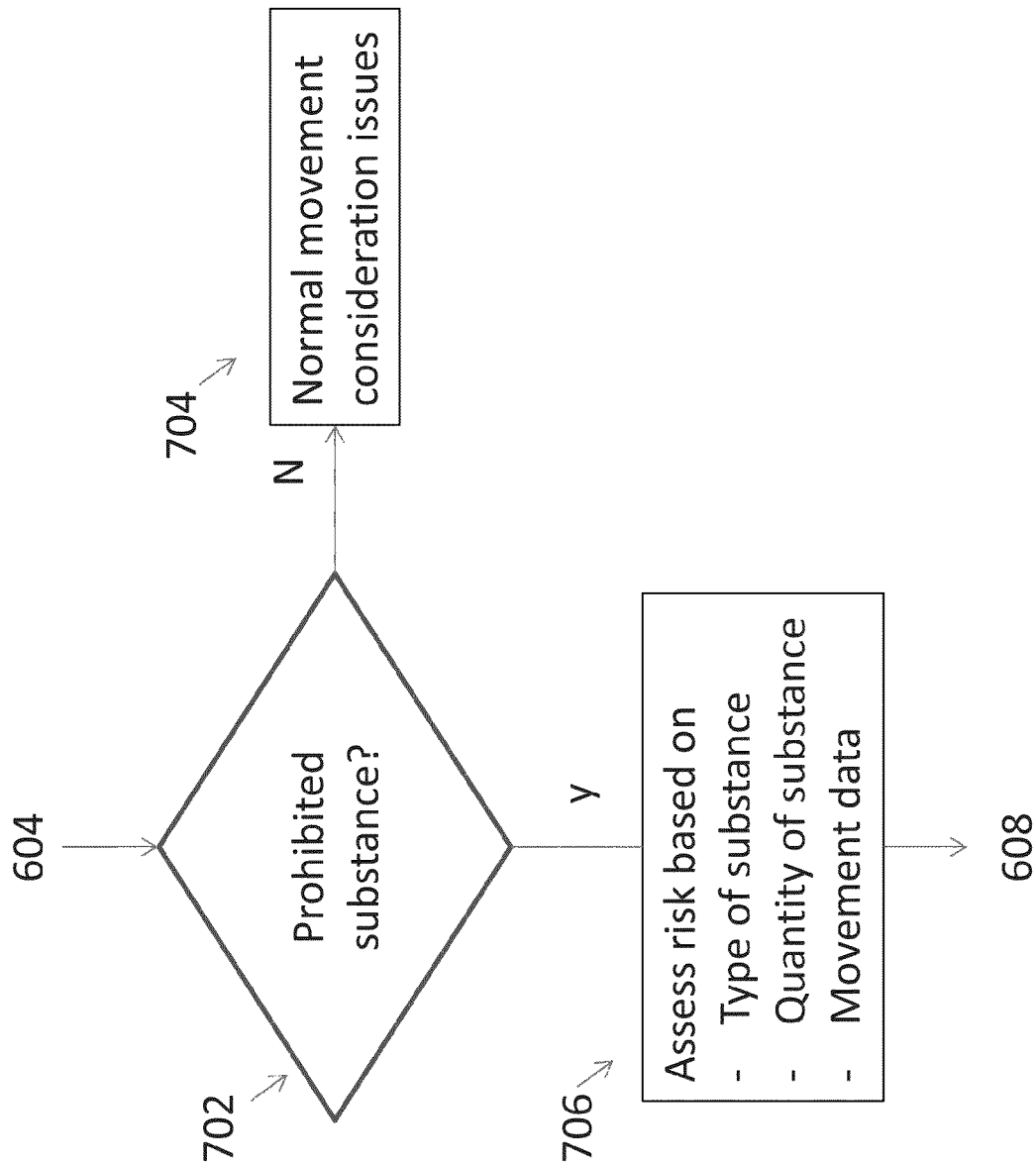
FIG. 7 illustrates a flowchart of operation of an embodiment of the invention.

Referring now to FIG. 7, a methodology of risk assessment from step 606 is shown in more detail. At step 702 the system will react to an indication of exposure to a prohibited substance; this step may range from an actual review of the data to as simple as reacting to a flag or marker in the data. If no substance is detected, then the system returns to its normal processing of movement data and other monitoring activities. If a substance is detected, at step 706 the system will assess the risk based on the nature of the detected substance, the amount/quantity amount of the substance, and/or the movement data for movement activity of the monitored person for a period of time prior to the screening. Control passes to step 608 for reporting the violation based on the assessed risk According to another embodiment of the invention, the central monitoring location 35 maintains or has access to information on mass transit routes. Movement data that reflects driving speed can be cross-referenced with mass transit information. If the movement data reflects a route of the monitored person that is consistent with a mass transit route while mass transit is in operation, then it would tend to indicate that drunk driving was not involved. The system could account for this at step 606 and 704 by discounting the possibility of driving in assessing the risk. In the example above, a 0.8 blood alcohol level when driving would be a high level alert, but if the movement was determined to be for mass transit it would only be a moderate level alert because it was outside the home but not driving. This might only be an alert to a parole officer for discretionary response, and thus avoid an alert to the local police that would essentially translate to a false alarm.

The embodiments herein are directed to monitoring a person by a locked personal monitoring device, but the invention is not so limited. Other embodiments include a non-locked device 12, or attaching the device to an object, in which the person responsible for the object is subject to substance abuse screening.

Tamper detection as provided for the various components may take a variety of forms. By way of non-limiting example, the tamper detection mechanism may include: i) signal continuity detection, ii) electrical, optical or electro-magnet switches or detectors that detect unauthorized opening and/or iii) electrical, thermal proximity devices which monitor the proximity to the individual. An accelerometer 115 can be provided for the stationary components to detect movement and/or relocation.

Figure 8:
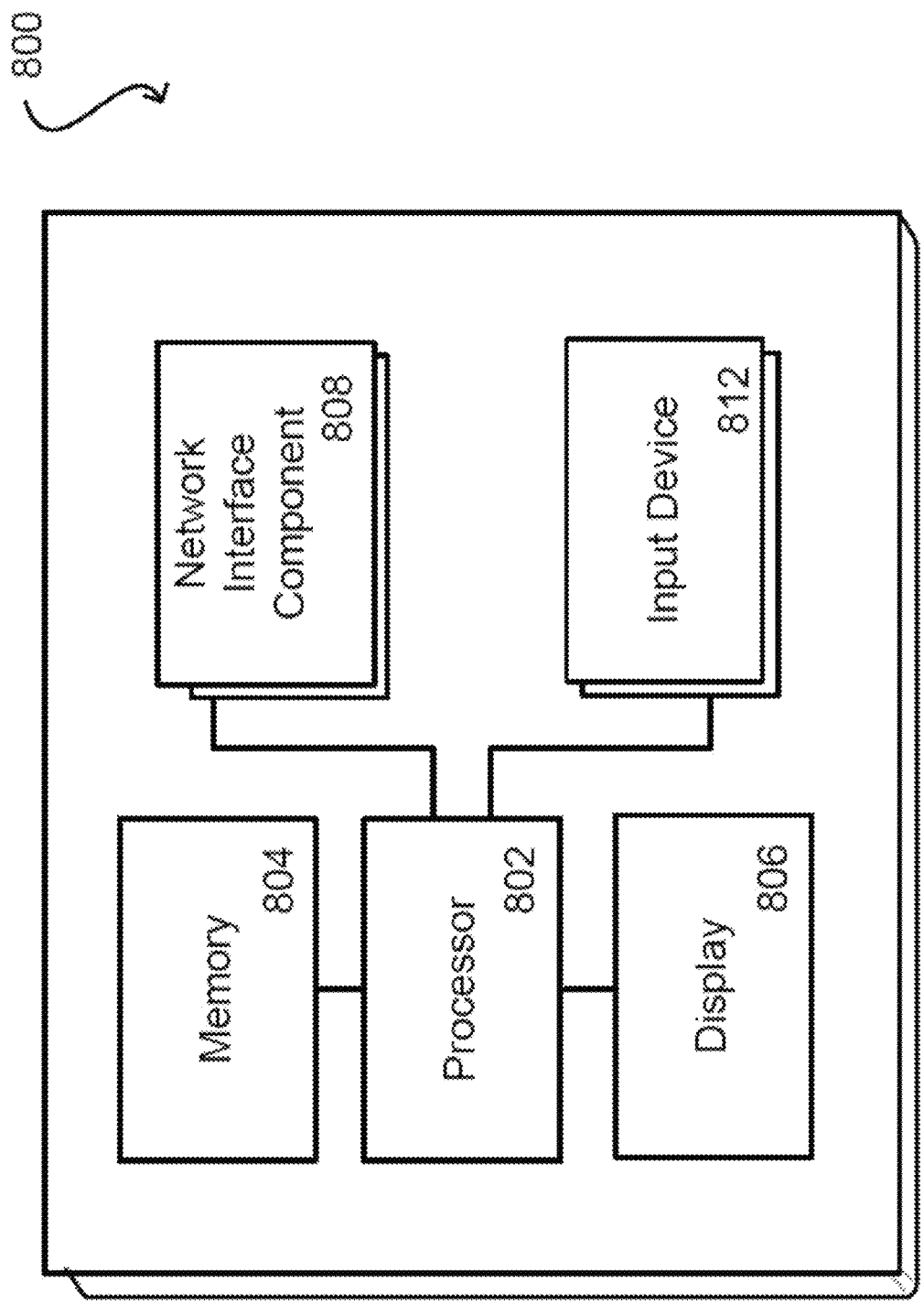
FIG. 8 illustrates computer aspects of various embodiments of the invention.

FIG. 8 illustrates a logical arrangement of a set of general components of an example computing device 800 as may be used in any of the component discussed herein. In this example, the device includes a processor 802 for executing instructions that can be stored in a memory device or element 804. As would be apparent to one of ordinary skill in the art, the device can include many types of memory, data storage, or non-transitory computer-readable storage media, such as a first data storage for program instructions for execution by the processor 802, a separate storage for images or data, a removable memory for sharing information with other devices, etc. The device typically will include some type of display element 806, such as a touch screen or liquid crystal display (LCD), and/or audio speakers. As discussed, the device in many embodiments will include at least one input element 808 able to receive conventional input from a user. This conventional input can include, for example, a push button, touch pad, touch screen, keyboard, mouse, keypad, or any other such device or element whereby a user can input a command to the device. In some embodiments, the computing device 800 of FIG. 8 can include one or more network interface elements 808 for communicating over various networks, such as a Wi-Fi, Bluetooth, RF, wired, or wireless communication systems. The device in many embodiments can communicate with a network, such as the Internet, and may be able to communicate with other such devices.

Each computing device typically will include an operating system that provides executable program instructions for the general administration and operation of that device and typically will include computer-readable medium storing instructions that, when executed by a processor of the server, allow the computing device to perform its intended functions. Suitable implementations for the operating system and general functionality of the servers are known or commercially available and are readily implemented by persons having ordinary skill in the art, particularly in light of the disclosure herein.

Various embodiments discussed or suggested herein can be implemented in a wide variety of operating environments, which in some cases can include one or more user computers, computing devices, or processing devices that can be used to operate any of a number of applications. User or client devices can include any of a number of general purpose personal computers, such as desktop or laptop computers running a standard operating system, as well as cellular, wireless, and handheld devices running mobile software and capable of supporting a number of networking and messaging protocols. Such a system also can include a number of workstations running any of a variety of commercially-available operating systems and other known applications for purposes such as development and database management. These devices also can include other electronic devices, such as dummy terminals, thin-clients, gaming systems, and other devices capable of communicating via a network.

Most embodiments utilize at least one network that would be familiar to those skilled in the art for supporting communications using any of a variety of commercially-available protocols, such as TCP/IP, OSI, FTP, UPnP, NFS, CIFS, and AppleTalk. The network can be, for example, a local area network, a wide-area network, a virtual private network, the Internet, an intranet, extranet, a public switched telephone network, an infrared network, a wireless network, and any combination thereof.

In embodiments where the computing device includes a Web server, the Web server can run any of a variety of server or mid-tier applications, including HTTP servers, FTP servers, CGI servers, data servers, Java servers, and business application servers. The server(s) also may be capable of executing programs or scripts in response requests from user devices, such as by executing one or more Web applications that may be implemented as one or more scripts or programs written in any programming language, such as Java®, C, C# or C++, or any scripting language, such as Perl, Python, or TCL, as well as combinations thereof. The server(s) may also include database servers, including without limitation those commercially available from Oracle®, Microsoft®, Sybase®, and IBM®.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers, or other network devices may be stored locally and/or remotely, as appropriate. Where a system includes computerized devices, each such device can include hardware elements that may be electrically coupled via a bus, the elements including, for example, at least one central processing unit (CPU), at least one input device (e.g., a mouse, keyboard, controller, touch screen, or keypad), and at least one output device (e.g., a display device, printer, or speaker). Such a system may also include one or more storage devices, such as disk drives, optical storage devices, and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.), and working memory as described above. The computer-readable storage media reader can be connected with, or configured to receive, a computer-readable storage medium, representing remote, local, fixed, and/or removable storage devices as well as storage media for temporarily and/or more permanently containing, storing, transmitting, and retrieving computer-readable information. The system and various devices also typically will include a number of software applications, modules, services, or other elements located within at least one working memory device, including an operating system and application programs, such as a client application or Web browser. It should be appreciated that alternate embodiments may have numerous variations from that described above. For example, customized hardware might also be used and/or particular elements might be implemented in hardware, software (including portable software, such as applets), or both. Further, connection to other computing devices such as network input/output devices may be employed.

Storage media and computer readable media for containing code, or portions of code, can include any appropriate media known or used in the art, including storage media and communication media, such as but not limited to volatile and non-volatile, removable and non-removable media implemented in any method or technology for storage and/or transmission of information such as computer readable instructions, data structures, program modules, or other data, including RAM, ROM, EEPROM, flash memory or other memory technology, CD-ROM, digital versatile disk (DVD) or other optical storage, magnetic cassettes, magnetic tape, magnetic disk storage or other magnetic storage devices, or any other medium which can be used to store the desired information and which can be accessed by a system device. Based on the disclosure and teachings provided herein, a person of ordinary skill in the art will appreciate other ways and/or methods to implement the various embodiments.

The use of "first", "second" ... as a modifier herein is to distinguish between different occurrences of similar terms, and does not imply any limits on number or order.

The specification and drawings are, accordingly, to be regarded in an illustrative rather than a restrictive sense. It will, however, be evident that various modifications and changes may be made thereunto without departing from the broader spirit and scope of the invention as set forth in the claims.

What is claimed is:

1. A method performed on electronic computer hardware in conjunction with software for determining a response to exposure of a monitored person to a prohibited substance, comprising:
   first receiving movement data representing movement of the monitored person over time;
   second receiving an indication that a monitored person has been exposed to a quantity of a prohibited substance;
   first determining, from the received movement data, movement activity of the monitored person for a period of time before the exposure was detected;
   second determining a risk parameter based on at least (a) the amount of the quantity of the prohibited substance, and (b) the movement activity;
   issuing a notice to a supervising authority in substantially real time when the second determining results in a risk parameter that is above a first threshold; and
   issuing a notice to a supervising authority in non-real time when the second determining results in a risk parameter that is below the first threshold;
   wherein the risk parameter represents a combined consideration of at least (a) the amount of the quantity of the prohibited substance, and (b) the movement activity;
   wherein the combined consideration comprises considering exposure to the prohibited substance when the monitored person was remote from a predetermined location during the period of time before exposure to be a greater risk relative to exposure to the prohibited substance when the movement activity indicates that the monitored person remained at the predetermined location during the period of time.

2. A method performed on electronic computer hardware in conjunction with software for determining a response to exposure of a monitored person to a prohibited substance, comprising:
   first receiving movement data representing movement of the monitored person over time;
   second receiving an indication that a monitored person has been exposed to a quantity of a prohibited substance;
   first determining, from the received movement data, movement activity of the monitored person for a period of time before the exposure was detected;
   second determining a risk parameter based on at least (a) the amount of the quantity of the prohibited substance, and (b) the movement activity;
   issuing a notice to a supervising authority in substantially real time when the second determining results in a risk parameter that is above a first threshold; and
   issuing a notice to a supervising authority in non-real time when the second determining results in a risk parameter that is below the first threshold;
   wherein the second determining comprises considering movement activity that indicates that the monitored person was moving between locations during the period of time as a greater risk compared to when the movement activity indicates that the monitored person remained at a single predetermined location during the period of time.

3. A method performed on electronic computer hardware in conjunction with software for determining a response to exposure of a monitored person to a prohibited substance, comprising:
   first receiving movement data representing movement of the monitored person over time;
   second receiving an indication that a monitored person has been exposed to a quantity of a prohibited substance;
   first determining, from the received movement data, movement activity of the monitored person for a period of time before the exposure was detected;
   second determining a risk parameter based on at least (a) the amount of the quantity of the prohibited substance, and (b) the movement activity;
   issuing a notice to a supervising authority in substantially real time when the second determining results in a risk parameter that is above a first threshold; and
   issuing a notice to a supervising authority in non-real time when the second determining results in a risk parameter that is below the first threshold;
   wherein the second determining comprises increasing the relevance of movement activity that indicates that the monitored individual was in a moving vehicle.

4. The method of claim 3, wherein the second determining further comprises, when the movement activity indicates that the monitored individual was in a moving vehicle:
   comparing the movement activity with at least one predetermined mass transit route;
   reducing the relevance of the movement activity when coincident with a mass transit route.

5. The method of claim 1, further comprising issuing a notice to an emergency authority in substantially real time when the second determining results in a risk parameter that is above a second threshold that is higher than the first threshold.

6. A computer program stored on a non-transitory computer readable medium for determining a response to exposure of a monitored person to a prohibited substance, the computer program comprising code for:
   first receiving movement data representing movement of the monitored person over time;
   second receiving an indication that a monitored person has been exposed to a quantity of a prohibited substance;
   first determining, from the received movement data, movement activity of the monitored person for a period of time before the exposure was detected;
   second determining a risk parameter based on at least (a) the amount of the quantity of the prohibited substance, and (b) the movement activity;
   issuing a notice to a supervising authority in substantially real time when the second determining results in a risk parameter that is above a first threshold; and
   issuing a notice to a supervising authority in non-real time when the second determining results in a risk parameter that is below the first threshold,
   wherein the risk parameter represents a combined consideration of at least (a) the amount of the quantity of the prohibited substance, and (b) the movement activity;
   wherein the combined consideration comprises considering exposure to the prohibited substance when the monitored person was remote from a predetermined location during the period of time before exposure to be a greater risk relative to exposure to the prohibited substance when the movement activity indicates that the monitored person remained at the predetermined location during the period of time.

7. A computer program stored on a non-transitory computer readable medium for determining a response to exposure of a monitored person to a prohibited substance, the computer program comprising code for:
   first receiving movement data representing movement of the monitored person over time;
   second receiving an indication that a monitored person has been exposed to a quantity of a prohibited substance;
   first determining, from the received movement data, movement activity of the monitored person for a period of time before the exposure was detected;
   second determining a risk parameter based on at least (a) the amount of the quantity of the prohibited substance, and (b) the movement activity;
   issuing a notice to a supervising authority in substantially real time when the second determining results in a risk parameter that is above a first threshold; and
   issuing a notice to a supervising authority in non-real time when the second determining results in a risk parameter that is below the first threshold,
   wherein the code for second determining comprises considering movement activity that indicates that the monitored person was moving between locations during the period of time as a greater risk compared to when the movement activity indicates that the monitored person remained at a single predetermined location during the period of time.

8. A computer program stored on a non-transitory computer readable medium for determining a response to exposure of a monitored person to a prohibited substance, the computer program comprising code for:
   first receiving movement data representing movement of the monitored person over time;
   second receiving an indication that a monitored person has been exposed to a quantity of a prohibited substance;
   first determining, from the received movement data, movement activity of the monitored person for a period of time before the exposure was detected;
   second determining a risk parameter based on at least (a) the amount of the quantity of the prohibited substance, and (b) the movement activity;
   issuing a notice to a supervising authority in substantially real time when the second determining results in a risk parameter that is above a first threshold; and
   issuing a notice to a supervising authority in non-real time when the second determining results in a risk parameter that is below the first threshold,
   wherein the second determining comprises increasing the relevance of movement activity that indicates that the monitored individual was in a moving vehicle.

9. The computer program stored on a non-transitory computer readable medium of claim 8, wherein the second determining further comprises, when the movement activity indicates that the monitored individual was in a moving vehicle:
   comparing the movement activity with at least one predetermined mass transit route;
   reducing the relevance of the movement activity when coincident with a mass transit route.

10. The computer program stored on a non-transitory computer readable medium of claim 6, further comprising issuing a notice to an emergency authority in substantially real time when the second determining results in a risk parameter that is above a second threshold that is higher than the first threshold.

11. An apparatus for monitoring and responding to exposure by a monitored person to a prohibited substance, comprising:
   an electronic computer processor;
   a memory storing instructions configured to execute on the processor to cause the processor to:
      first receive movement data representing movement of the monitored person over time;
      second receive an indication that a monitored person has been exposed to a quantity of a prohibited substance;
      first determine, from the received movement data, movement activity of the monitored person for a period of time before the exposure was detected;
      second determine a risk parameter based on at least (a) the amount of the quantity of the prohibited substance, and (b) the movement activity;
      issue a notice to a supervising authority in substantially real time when the second determining results in a risk parameter that is above a first threshold; and
      issue a notice to a supervising authority in non-real time when the second determining results in a risk parameter that is below the first threshold,
      wherein the risk parameter represents a combined consideration of at least (a) the amount of the quantity of the prohibited substance, and (b) the movement activity;
      wherein the combined consideration comprises considering exposure to the prohibited substance when the monitored person was remote from a predetermined location during the period of time before exposure to be a greater risk relative to exposure to the prohibited substance when the movement activity indicates that the monitored person remained at the predetermined location during the period of time.

12. An apparatus for monitoring and responding to exposure by a monitored person to a prohibited substance, comprising:
   an electronic computer processor;
   a memory storing instructions configured to execute on the processor to cause the processor to:
      first receive movement data representing movement of the monitored person over time;
      second receive an indication that a monitored person has been exposed to a quantity of a prohibited substance;
      first determine, from the received movement data, movement activity of the monitored person for a period of time before the exposure was detected;
      second determine a risk parameter based on at least (a) the amount of the quantity of the prohibited substance, and (b) the movement activity;
      issue a notice to a supervising authority in substantially real time when the second determining results in a risk parameter that is above a first threshold; and
      issue a notice to a supervising authority in non-real time when the second determining results in a risk parameter that is below the first threshold,
   wherein the second determining comprises considering movement activity that indicates that the monitored person was moving between locations during the period of time as a greater risk compared to when the movement activity indicates that the monitored person remained at a single predetermined location during the period of time.

13. An apparatus for monitoring and responding to exposure by a monitored person to a prohibited substance, comprising:
an electronic computer processor;
a memory storing instructions configured to execute on the processor to cause the processor to:
first receive movement data representing movement of the monitored person over time;
second receive an indication that a monitored person has been exposed to a quantity of a prohibited substance;
first determine, from the received movement data, movement activity of the monitored person for a period of time before the exposure was detected;
second determine a risk parameter based on at least (a) the amount of the quantity of the prohibited substance, and (b) the movement activity;
issue a notice to a supervising authority in substantially real time when the second determining results in a risk parameter that is above a first threshold; and
issue a notice to a supervising authority in non-real time when the second determining results in a risk parameter that is below the first threshold,
wherein the second determining comprises increasing the relevance of movement activity that indicates that the monitored individual was in a moving vehicle.

14. The apparatus of claim 13, wherein the determining further comprises, when the movement activity indicates that the monitored individual was in a moving vehicle:
comparing the movement activity with at least one predetermined mass transit route;
reducing the relevance of the movement activity when coincident with a mass transit route.

15. The apparatus of claim 11, further comprising issuing a notice to an emergency authority in substantially real time when the second determining results in a risk parameter is above a second threshold that is higher than the first threshold.

* * * * *